(12) United States Patent
Baril et al.

(10) Patent No.: US 11,510,749 B2
(45) Date of Patent: Nov. 29, 2022

(54) INSERTABLE CUTTING GUARD

(71) Applicant: Covidien LP, Mansfield, MA (US)

(72) Inventors: Jacob C. Baril, Norwalk, CT (US); Amy L. Kung, Hamden, CT (US); Saumya Banerjee, Hamden, CT (US)

(73) Assignee: COVIDIEN LP, Mansfield, MA (US)

( * ) Notice: Subject to any disclaimer, the term of this patent is extended or adjusted under 35 U.S.C. 154(b) by 252 days.

(21) Appl. No.: 16/883,311

(22) Filed: May 26, 2020

(65) Prior Publication Data
US 2021/0369385 A1    Dec. 2, 2021

(51) Int. Cl.
*A61B 90/00* (2016.01)
*A61B 17/34* (2006.01)

(52) U.S. Cl.
CPC .......... *A61B 90/08* (2016.02); *A61B 17/3423* (2013.01); *A61B 2017/346* (2013.01); *A61B 2090/036* (2016.02); *A61B 2090/08021* (2016.02)

(58) Field of Classification Search
CPC ........ A61B 17/3423; A61B 2017/3425; A61B 2017/3427; A61B 2017/346; A61B 2017/3416; A61B 90/08; A61B 2090/036; A61B 2090/08021
See application file for complete search history.

(56) References Cited

U.S. PATENT DOCUMENTS

| | | | |
|---|---|---|---|
| 5,643,283 A | 7/1997 | Younker | |
| 6,059,793 A | 5/2000 | Pagedas | |
| 6,156,055 A | 12/2000 | Ravenscroft | |
| 6,162,209 A | 12/2000 | Gobron et al. | |
| 6,171,317 B1 | 1/2001 | Jackson et al. | |
| 6,206,889 B1 | 3/2001 | Bennardo | |
| 6,224,612 B1 | 5/2001 | Bates et al. | |
| 6,228,095 B1 | 5/2001 | Dennis | |
| 6,248,113 B1 | 6/2001 | Fina | |
| 6,258,102 B1 | 7/2001 | Pagedas | |
| 6,264,663 B1 | 7/2001 | Cano | |
| 6,270,505 B1 | 8/2001 | Yoshida et al. | |
| 6,280,451 B1 | 8/2001 | Bates et al. | |
| 6,344,026 B1 | 2/2002 | Burbank et al. | |
| 6,350,266 B1 | 2/2002 | White et al. | |
| 6,350,267 B1 | 2/2002 | Stefanchik | |
| 6,358,198 B1 | 3/2002 | Levin et al. | |
| 6,368,328 B1 | 4/2002 | Chu et al. | |
| 6,383,195 B1 | 5/2002 | Richard | |

(Continued)

FOREIGN PATENT DOCUMENTS

| | | |
|---|---|---|
| WO | 2004002334 A1 | 1/2004 |
| WO | 2014158880 A1 | 10/2014 |

*Primary Examiner* — Ashley L Fishback
(74) *Attorney, Agent, or Firm* — Carter, DeLuca & Farrell LLP

(57) ABSTRACT

A tissue guard includes a body having a proximal end and a distal end and defining a lumen therethrough. The distal end has a long petal and a short petal disposed in substantial opposition relative to one another and the short petal is configured to move between a first position wherein the short petal is disposed within the lumen to facilitate insertion of the long petal within an incision and a second position wherein the short petal is extended relative to the lumen and in substantial opposition to the long petal to facilitate retention of the tissue guard within the incision.

27 Claims, 3 Drawing Sheets

(56) References Cited

U.S. PATENT DOCUMENTS

| | | |
|---|---|---|
| 6,383,197 B1 | 5/2002 | Conlon et al. |
| 6,387,102 B2 | 5/2002 | Pagedas |
| 6,406,440 B1 | 6/2002 | Stefanchik |
| 6,409,733 B1 | 6/2002 | Conlon et al. |
| 6,447,523 B1 | 9/2002 | Middleman et al. |
| 6,530,923 B1 | 3/2003 | Dubrul et al. |
| 6,537,273 B1 | 3/2003 | Sosiak et al. |
| 6,752,822 B2 | 6/2004 | Jespersen |
| 6,805,699 B2 | 10/2004 | Shimm |
| 6,951,533 B2 | 10/2005 | Foley |
| 6,986,774 B2 | 1/2006 | Middleman et al. |
| 7,037,275 B1 | 5/2006 | Marshall et al. |
| 7,052,501 B2 | 5/2006 | McGuckin, Jr. |
| 7,087,062 B2 | 8/2006 | Dhindsa |
| 7,101,379 B2 | 9/2006 | Gregory, Jr. et al. |
| 7,101,380 B2 | 9/2006 | Khachin et al. |
| 7,112,172 B2 | 9/2006 | Orban, III et al. |
| 7,115,125 B2 | 10/2006 | Nakao et al. |
| 7,144,400 B2 | 12/2006 | Byrum et al. |
| 7,169,154 B1 | 1/2007 | Que et al. |
| 7,229,418 B2 | 6/2007 | Burbank et al. |
| 7,285,126 B2 | 10/2007 | Sepetka et al. |
| 7,316,692 B2 | 1/2008 | Huffmaster |
| 7,357,801 B2 | 4/2008 | Burbank et al. |
| 7,534,252 B2 | 5/2009 | Sepetka et al. |
| 7,547,310 B2 | 6/2009 | Whitfield |
| 7,615,013 B2 | 11/2009 | Clifford et al. |
| 7,618,437 B2 | 11/2009 | Nakao |
| 7,645,283 B2 | 1/2010 | Reynolds et al. |
| 7,670,346 B2 | 3/2010 | Whitfield |
| 7,678,118 B2 | 3/2010 | Bates et al. |
| 7,722,626 B2 | 5/2010 | Middleman et al. |
| 7,727,227 B2 | 6/2010 | Teague et al. |
| 7,731,722 B2 | 6/2010 | Lavelle et al. |
| 7,731,723 B2 | 6/2010 | Kear et al. |
| 7,762,959 B2 | 7/2010 | Bilsbury |
| 7,762,960 B2 | 7/2010 | Timberlake et al. |
| 7,875,038 B2 | 1/2011 | Que et al. |
| 7,892,242 B2 | 2/2011 | Goldstein |
| 7,914,540 B2 | 3/2011 | Schwartz et al. |
| 7,918,860 B2 | 4/2011 | Leslie et al. |
| 7,955,292 B2 | 6/2011 | Leroy et al. |
| 8,057,485 B2 | 11/2011 | Hollis et al. |
| 8,075,567 B2 | 12/2011 | Taylor et al. |
| 8,118,816 B2 | 2/2012 | Teague |
| 8,152,820 B2 | 4/2012 | Mohamed et al. |
| 8,172,772 B2 | 5/2012 | Zwolinski et al. |
| 8,211,115 B2 | 7/2012 | Cheng et al. |
| 8,282,572 B2 | 10/2012 | Bilsbury |
| 8,337,510 B2 | 12/2012 | Rieber et al. |
| 8,348,827 B2 | 1/2013 | Zwolinski |
| 8,409,216 B2 | 4/2013 | Parihar et al. |
| 8,414,596 B2 | 4/2013 | Parihar et al. |
| 8,419,749 B2 | 4/2013 | Shelton, IV et al. |
| 8,425,533 B2 | 4/2013 | Parihar et al. |
| 8,430,826 B2 | 4/2013 | Uznanski et al. |
| 8,435,237 B2 | 5/2013 | Bahney |
| 8,444,655 B2 | 5/2013 | Parihar et al. |
| 8,486,087 B2 | 7/2013 | Fleming |
| 8,512,351 B2 | 8/2013 | Teague |
| 8,579,914 B2 | 11/2013 | Menn et al. |
| 8,585,712 B2 | 11/2013 | O'Prey et al. |
| 8,591,521 B2 | 11/2013 | Cherry et al. |
| 8,652,147 B2 | 2/2014 | Hart |
| 8,721,658 B2 | 5/2014 | Kahle et al. |
| 8,734,464 B2 | 5/2014 | Grover et al. |
| 8,777,961 B2 | 7/2014 | Cabrera et al. |
| 8,795,291 B2 | 8/2014 | Davis et al. |
| 8,821,377 B2 | 9/2014 | Collins |
| 8,827,968 B2 | 9/2014 | Taylor et al. |
| 8,870,894 B2 | 10/2014 | Taylor et al. |
| 8,906,035 B2 | 12/2014 | Zwolinski et al. |
| 8,956,370 B2 | 2/2015 | Taylor et al. |
| 8,968,329 B2 | 3/2015 | Cabrera |
| 8,986,321 B2 | 3/2015 | Parihar et al. |
| 9,005,215 B2 | 4/2015 | Grover et al. |
| 9,017,328 B2 | 4/2015 | Bahney |
| 9,017,340 B2 | 4/2015 | Davis |
| 9,033,995 B2 | 5/2015 | Taylor et al. |
| 9,084,588 B2 | 7/2015 | Farascioni |
| 9,101,342 B2 | 8/2015 | Saleh |
| 9,113,848 B2 | 8/2015 | Fleming et al. |
| 9,113,849 B2 | 8/2015 | Davis |
| 9,308,008 B2 | 4/2016 | Duncan et al. |
| 9,364,201 B2 | 6/2016 | Orban, III |
| 9,364,202 B2 | 6/2016 | Menn et al. |
| 9,370,341 B2 | 6/2016 | Ceniccola et al. |
| 9,370,378 B2 | 6/2016 | O'Prey et al. |
| 9,375,224 B2 | 6/2016 | Jansen |
| 9,414,817 B2 | 8/2016 | Taylor et al. |
| 9,468,452 B2 | 10/2016 | Menn et al. |
| 9,486,188 B2 | 11/2016 | Secrest et al. |
| 9,522,034 B2 | 12/2016 | Johnson et al. |
| 9,549,747 B2 | 1/2017 | Carlson |
| 9,579,115 B2 | 2/2017 | Kahle et al. |
| 9,592,067 B2 | 3/2017 | Hartoumbekis |
| 9,622,730 B2 | 4/2017 | Farascioni |
| 9,629,618 B2 | 4/2017 | Davis et al. |
| 9,642,638 B1 | 5/2017 | Carrier |
| 9,655,644 B2 | 5/2017 | Collins |
| 9,730,716 B2 | 8/2017 | Secrest et al. |
| 9,789,268 B2 | 10/2017 | Hart et al. |
| 9,808,228 B2 | 11/2017 | Kondrup et al. |
| 9,826,997 B2 | 11/2017 | Cherry et al. |
| 9,867,600 B2 | 1/2018 | Parihar et al. |
| 9,877,893 B2 | 1/2018 | Taylor et al. |
| 2008/0234550 A1* | 9/2008 | Hawkes ............ A61B 17/3462 606/108 |
| 2011/0201893 A1* | 8/2011 | O'Prey ............ A61B 17/3423 600/206 |
| 2017/0224321 A1* | 8/2017 | Kessler ............ A61B 17/3211 |

* cited by examiner

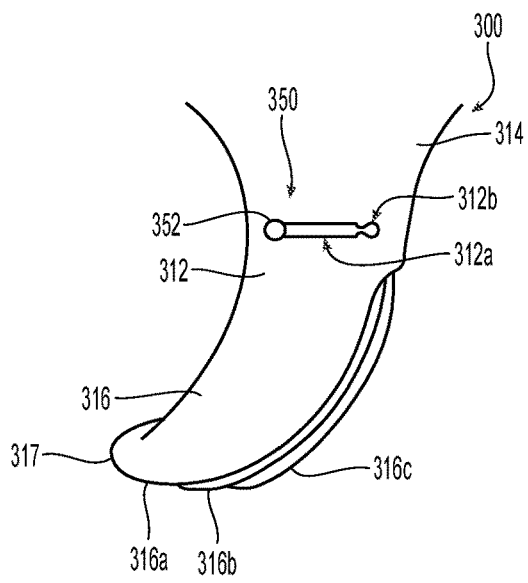
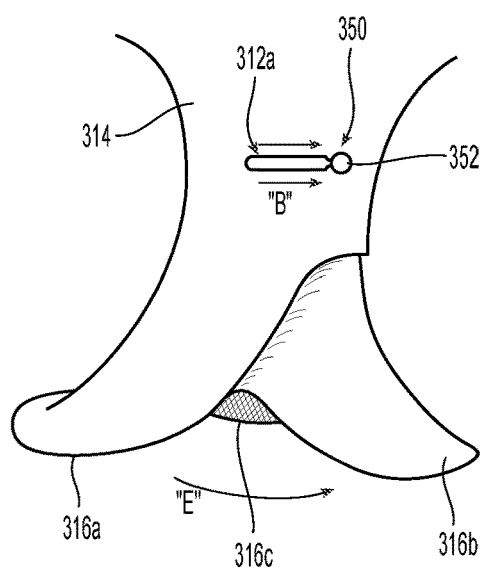
*Fig. 4A*  *Fig. 4B*
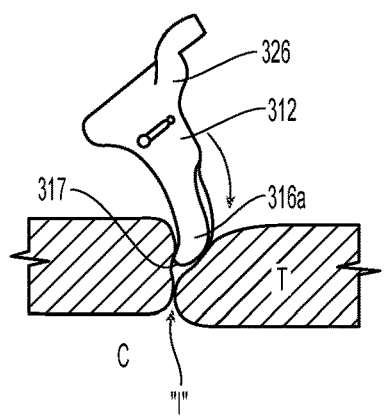
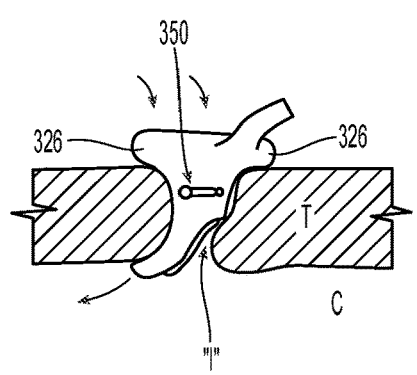
*Fig. 5A*  *Fig. 5B*
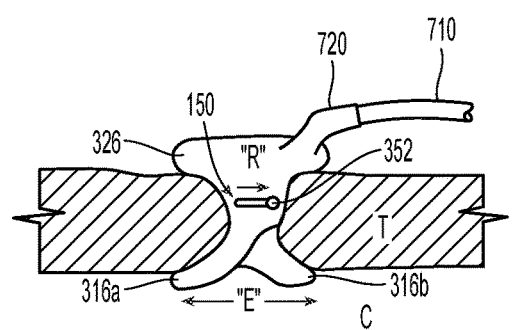
*Fig. 5C*

INSERTABLE CUTTING GUARD

FIELD

The present disclosure relates to tissue specimen removal and, more particularly, to tissue guards and systems incorporating the same for use in tissue specimen removal procedures and other electrosurgical surgical procedures.

BACKGROUND

In minimally-invasive surgical procedures, operations are carried out within an internal body cavity through small entrance openings in the body. The entrance openings may be natural passageways of the body or may be surgically created, for example, by making a small incision into which a cannula is inserted.

Minimally-invasive surgical procedures may be used for partial or total removal of tissue from an internal body cavity. However, the restricted access provided by minimally-invasive openings (natural passageways and/or surgically created openings) presents challenges with respect to maneuverability and visualization. The restricted access also presents challenges when large tissue specimens are required to be removed. As such, tissue specimens that are deemed too large for intact removal may be broken down into a plurality of smaller pieces to facilitate removal from the internal body cavity. Typically electrosurgical instruments such as bipolar electrosurgical pencils may be utilized for this purpose.

SUMMARY

As used herein, the term "distal" refers to the portion that is described which is further from a user, while the term "proximal" refers to the portion that is being described which is closer to a user. Further, any or all of the aspects described herein, to the extent consistent, may be used in conjunction with any or all of the other aspects described herein.

Provided in accordance with aspects of the present disclosure is a tissue guard having a body including a proximal end and a distal end and defining a lumen therethrough. The distal end includes a long petal and a short petal disposed in substantial opposition relative to one another. The short petal is configured to move between a first position wherein the short petal is disposed within the lumen to facilitate insertion of the long petal within an incision and a second position wherein the short petal is extended relative to the lumen and in substantial opposition to the long petal to facilitate retention of the tissue guard within the incision.

In aspects according to the present disclosure, the short petal is selectively invertable within the lumen. In other aspects according to the present disclosure, the long petal is shaped like a shoe horn and is configured to pry the incision open upon insertion therein.

In aspects according to the present disclosure, the short petal is shaped like a shoe horn when extended relative to the lumen. In other aspects according to the present disclosure, the proximal end of the body is configured to remain outside the incision.

In aspects according to the present disclosure, after insertion of the long petal within the incision, the short petal is selectively extendible from the lumen to engage tissue opposite the long petal to facilitate retention of the tissue guard. In aspects according to the present disclosure, the short petal is reverted from within the lumen to extend the short petal to engage tissue opposite the long petal to facilitate retention of the tissue guard.

In aspects according to the present disclosure, the short petal is rotated from within the lumen to extend the short petal to engage tissue opposite the long petal to facilitate retention of the tissue guard. In other aspects according to the present disclosure, the short petal cooperates with a slide bolt disposed in a slot defined within the body of the tissue guard to selectively rotate and extend the short petal to engage tissue opposite the long petal to facilitate retention of the tissue guard. In yet other aspects according to the present disclosure, the slot includes a neck defined therein to lock the slide bolt when the short petal is disposed in one of the first or second positions.

In aspects according to the present disclosure, two short petals are disposed within the lumen when the short petals are disposed in the first position, the short petals disposed in stacked relation relative to one another and the long petal. In other aspects according to the present disclosure, the short petals and the long petal form a tri-pod arrangement when the short petals are disposed in the second position.

Provided in accordance with other aspects of the present disclosure is a tissue guard having a body including a proximal end and a distal end and defining a lumen therethrough, the distal end including a long petal and a short petal disposed in substantial opposition relative to one another. The short petal is configured to move between a first position wherein the short petal is inverted within the lumen to facilitate insertion of the long petal within an incision and a second position wherein the short petal is reverted relative to the lumen and extended in substantial opposition to the long petal to facilitate retention of the tissue guard within the incision.

Provided in accordance with aspects of the present disclosure is a tissue guard having a body including a proximal end and a distal end and defining a lumen therethrough, the distal end including a long petal and two short petals. The short petals are configured to move between a first position wherein the short petals are disposed within the lumen in stacked relation relative to one another and relative to the long petal to facilitate insertion of the long petal within an incision and a second position wherein the short petals are rotated from within the lumen to extend the short petals to engage tissue opposite the long petal to facilitate retention of the tissue guard.

In aspects according to the present disclosure, the short petals and the long petal form a tri-pod arrangement when the short petals are disposed in the second position. In other aspects according to the present disclosure, the short petals cooperate with a slide bolt disposed in a slot defined within the body of the tissue guard to selectively rotate and extend the short petals to engage tissue opposite the long petal to facilitate retention of the tissue guard. In yet other aspects according to the present disclosure, the slot includes a neck defined therein to lock the slide bolt when the short petals are disposed in one of the first or second positions.

BRIEF DESCRIPTION OF THE DRAWINGS

The above and other aspects and features of the present disclosure will become more apparent in light of the following detailed description when taken in conjunction with the accompanying drawings wherein like reference numerals identify similar or identical elements.

FIG. 4A is a side view of another embodiment of an insertable tissue guard in accordance with the present disclosure shown in a pre-insertion configuration;

FIG. 4B is a side view of the tissue guard of FIG. 4A shown in an expanded configuration; and FIGS. 5A-5C show various views of the tissue guard of FIGS. 4A-4B prior to, during and after insertion within an incision.

DETAILED DESCRIPTION

Figure 1A:
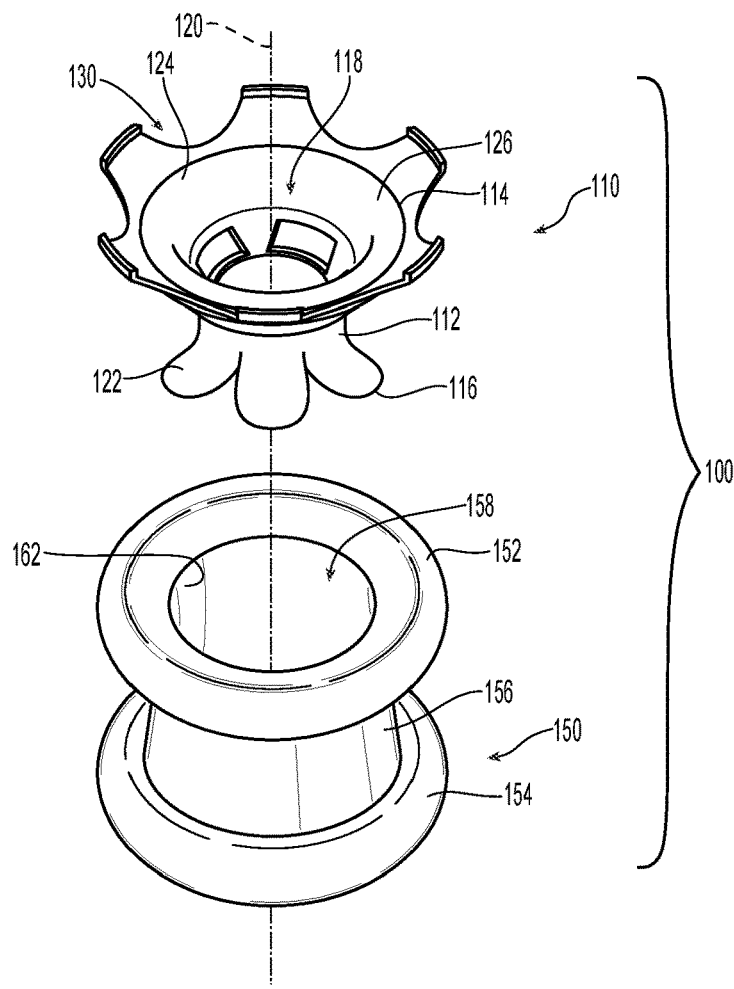
FIG. 1A is an exploded, top, perspective view of a prior art an access device and a tissue guard.
Figure 1B:
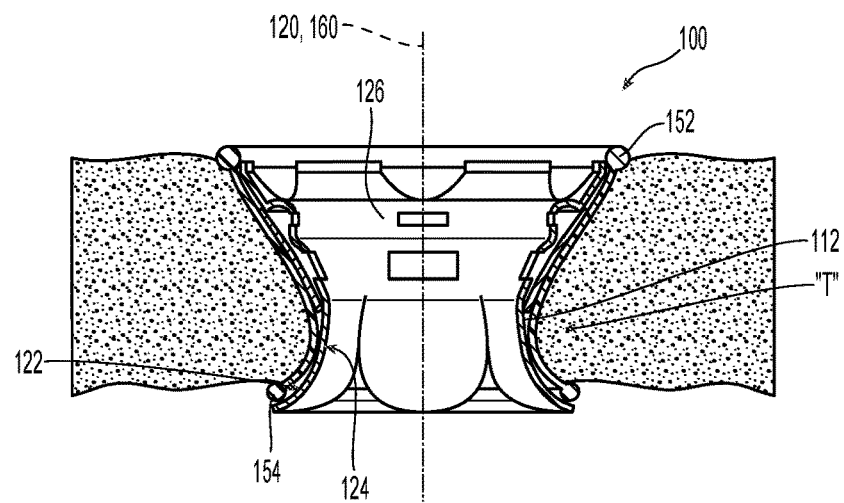
FIG. 1B is a cross-sectional view of the access device and tissue guard of FIG. 1A shown assembled and disposed within an opening in tissue.

Turning to FIGS. 1A and 1B, a prior art system 100 is shown and includes a tissue guard 110 and an access device 150. Tissue guard 110 is monolithically formed as a single piece of material, e.g., a biocompatible plastic such as, for example, polyethylene, polycarbonate, etc., from any suitable method, e.g., injection molding. The material, thickness, and configuration of tissue guard 110 are such that tissue guard 110 defines sufficient stiffness to maintain its shape when positioned within an opening in tissue "T" and/or when engaged within access device 150. However, the material, thickness, and configuration of tissue guard 110 also provide sufficient resilient flexibility to permit manipulation of tissue guard 110 from an at-rest position for insertion into an opening in tissue "T" and/or for engagement within access device 150, with tissue guard 110 returning to or towards the at-rest position after insertion and/or engagement as explained in more detail below. Further, the material, thickness, and configuration of tissue guard 110 is selected such that tissue guard 110 is configured to withstand cutting and puncturing by surgical knives, scalpels, pencils, and the like, thereby protecting surrounding tissue "T" and/or access device 150 from being cut or punctured. Tissue guard 110 may additionally or alternatively be configured to inhibit transfer of thermal and/or electrical energy therethrough to protect surrounding tissue "T" and/or access device 150 from thermal and/or electrical energy.

Continuing with reference to FIGS. 1A and 1B, tissue guard 110 includes a body 112 defining an open proximal end 114, an open distal end 116, and a lumen 118 extending therethrough between open proximal and distal ends 114, 116, respectively. Lumen 118 defines a longitudinal axis 120 and is configured to receive one or more surgical instruments (not shown) therethrough. In embodiments, body 112 defines a funnel-shaped configuration wherein a diameter of body 112 at open proximal end 114 thereof is greater than a diameter of body 112 at open distal end 116 thereof. Additionally or alternatively, the exterior surface 122 of body 112 may define a generally concave configuration while the interior surface 124 of body 112, which defines lumen 118, may define a generally convex configuration. One or more flanges 126 are configured to secure the tissue guard to the access device 150.

Access device 150 may be configured as a tissue retractor, an access port, or other suitable access device configured for positioning within an opening in tissue "T," e.g., a surgical incision or a naturally-occurring orifice, to provide access therethrough into an internal surgical site. Access device 150 includes a proximal rim 152 configured for positioning on an external side of the opening in tissue "T," a distal rim 154 configured for positioning on an internal side of the opening in tissue "T," and a body 156 extending between proximal and distal rims 152, 154, respectively. Body 156 is configured to extend through the opening in tissue "T" and defines a passageway 158 extending longitudinally therethrough to permit access to an internal surgical site through the opening in tissue "T." Passageway 158 defines a longitudinal axis 160. At least a portion of body 156 of access device 150 may be flexible to facilitate insertion and positioning of access device 150 within the opening in tissue "T." In embodiments, body 156 is formed from a flexible sleeve of material including one or more layers of material. Further, access device 150 may be selectively adjustable, e.g., by rolling proximal rim 154 distally about body 156, to retract tissue "T" and/or secure access device 150 within the opening in tissue "T." Access device 150 may further define an inwardly-extending overhang 162 between proximal rim 154 and body 156 and extending annularly about passageway 158.

As shown in FIG. 1B, in use, access device 150 is positioned within an opening in tissue "T" such that, as noted above, distal rim 154 is disposed on an internal surface of tissue "T" on the internal side of the opening in tissue "T," body 156 extends through the opening in tissue "T," and proximal rim 152 is disposed on an exterior surface of tissue "T" on the external side of the opening in tissue "T." As also noted above, access device 150 may be adjusted to conform access device 150 to a patient's anatomy, retracting tissue "T" and/or securing access device 150 within the opening in tissue "T." With access device 150 disposed within the opening in tissue "T," tissue guard 110, led by open distal end 116 thereof, is inserted into passageway 158.

Figure 2A:
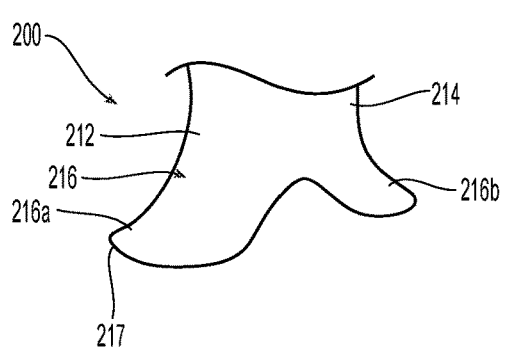
FIG. 2A is a side view of an insertable tissue guard in accordance with the present disclosure shown in an expanded configuration after insertion within an access device.
Figure 2B:
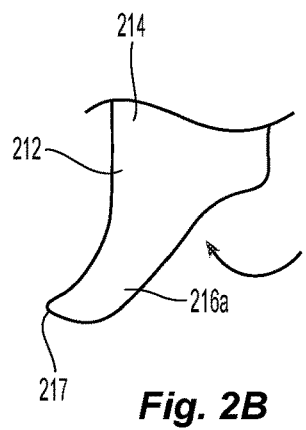
FIG. 2B is a side view of the tissue guard of FIG. 2A shown in an inverted, pre-insertion configuration.
Figure 2C:
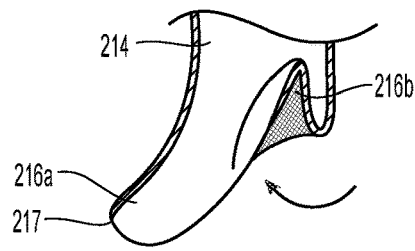
FIG. 2C is side, cross-sectional view of the tissue guard shown in FIG. 2B.

Turning now to FIGS. 2A-2C, one embodiment of a tissue guard for use with an electrosurgical pencil is shown and is generally identified as tissue guard 200. Tissue guard 200 is similar to tissue guard 110 described above and, as such, only those elements that differ are described in detail below. Referenced herein is made to an electrosurgical pencil that is only generally described and only those features necessary for a understanding of the overall system are provided in detail. Cross reference is made to various electrosurgical pencils that may be utilized with system 10, for example, U.S. patent application Ser. No. 16/776,922 filed Jan. 30, 2020, U.S. patent application Ser. No. 16/540,593 filed Aug. 14, 2019, U.S. patent application Ser. No. 16/781,557 filed Feb. 4, 2020 and U.S. patent application Ser. No. 16/789,553 filed Feb. 13, 2020 the entire contents of each of which being incorporated by reference herein.

Tissue guard 200 includes a proximal portion 214 which is configured for engagement with an access device, for example, access device 150, an elongated body portion 212 and a distal end 216 configured for insertion within the access device 150 or direct insertion within an incision "I" in tissue "T". One or more flanges 226 are configured to engage the proximal rim 152 of the access device 150 to secure the tissue guard 200 therein.

Figure 3A:
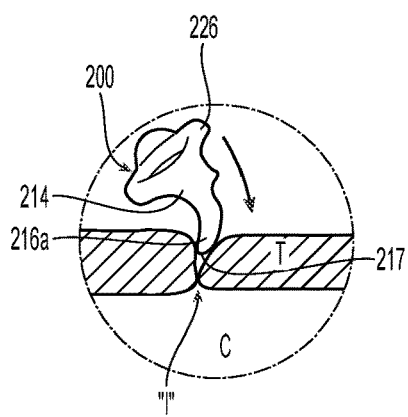
FIGS. 3A-3C show various views of the tissue guard of FIGS. 2A-2C prior to, during and after insertion within an incision.

Distal end 216 is generally oblong and includes a long petal 216a on one side thereof and a short petal 216b on an opposite side thereof to facilitate insertion of the tissue guard 200 into the access device 150 and an internal body cavity "C" (FIGS. 2A and 3A). Prior to insertion, short petal 216b is inverted into body 212 in the direction of the arrow "In" such that only the long petal 216a remains exposed for insertion (FIG. 2B).

Short petal 216b may include a break line or snap point which is a point where the short petal 216b inverts on itself and into the body 212. In other words, once the user pushes the short petal 216b into the body 212 passed a certain point, the short petal 216b inverts onto itself and tucks within the inner periphery of the body 212. Likewise, when the user pushes the short petal 216b outwardly from the body 212 after insertion, the short petal 216b automatically reverses back or reverts to the expanded configuration to engage the underside of the tissue "T" and secure the tissue guard 200.

Both the long petal 216a and the short petal 216b are configured in the shape of shoe-horns or duck-like flanges to facilitate insertion and retention thereof when engage against tissue "T". In other words, the shape of the petals 216a, 216b include a generally tapered, spoon-like distal edge to facilitate both insertion into an incision "I" in tissue "T" (e.g., petal 216a) and retention against the tissue "T" once inserted.

Figure 3B:
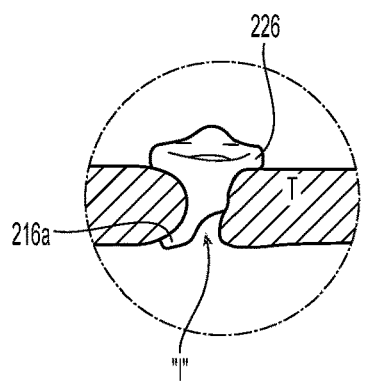
Figure 3C:
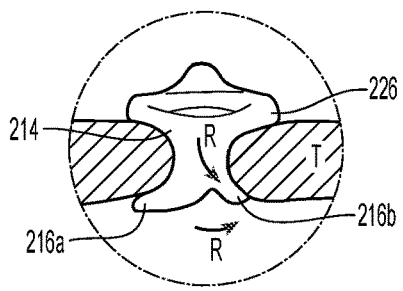

FIGS. 3A-3C show the tissue guard being inserted within an incision "I" in tissue "T". Prior to insertion, the short petal 216b of the tissue guard 200 is initially inverted to reduce the profile of the tissue guard 200 and to facilitate insertion. The long petal 216a is then inserted into the incision "I" and slipped through the incision "I" in a manner to pry open the incision "I" like a shoe-horn (FIG. 3B). Once seated within the incision "I" with the proximal flange 226 flush against the external side of tissue "T", the surgeon inserts an instrument (or finger) into the tissue guard 200 to push and rotate the short petal 216b outwardly in the direction "R" to engage the opposite side of tissue "T" within incision "I" (FIG. 3C). This seats the tissue guard 200 within the access device 150 in a more balanced fashion and provides opposing retention for the tissue guard 200 therein. As mentioned above, the shoe-horn or duck-bill shape of the petals 216a, 216b facilitate retention of the tissue guard 200 within the access device 150 in the incision "I".

FIGS. 4A and 4B show another embodiment of a tissue guard 300 in accordance with the present disclosure. Tissue guard 300 includes a proximal portion 314 which is configured for engagement with an access device, for example, access device 150, an elongated body portion 312 and a distal end 316 configured for insertion within the access device 150 or directly within an incision "I" in tissue "T". One or more flanges 326 (FIGS. 5A-5C) are configured to engage the proximal rim 152 of the access device 150 to secure the tissue guard 300 therein.

Distal end 316 is generally oblong and includes a long petal 316a on one side thereof and one or more short petals 316b and 316c on an opposite side thereof to facilitate insertion of the tissue guard 300 into the access device 150 or incision "I" of an internal body cavity "C" (FIGS. 5A-5C). The long petal 316a and the short petals 316b, 316c may be arranged in a tri-pod like manner or in a substantially equally-disposed manner about the distal end 316 of the tissue guard 300 to provide balanced retention thereof within the access device 150 or directly within tissue.

Short petals 316b, 316c are configured to rotate between a first position disposed within the tissue guard 300 in stacked or layered relation under petal 316a (FIG. 4A) and a second position wherein the short petals 316b, 316c extend or rotate into the above-mentioned tri-pod configuration (FIG. 4B) in the direction of arrow "E". More particularly, tissue guard 300 includes a slot 312a defined in the body 312 thereof that is configured to receive a slide bolt 352 which, in turn, mechanically engages each short petal 316b, 316c. Actuation of the slide bolt 352 in the direction "S" rotates or extends the short petals 316b, 316c between the stacked configuration and the tri-pod configuration. Slot 312a may include a locking feature, e.g., neck 312b, defined therein which locks the slide bolt 352 therein which, in turn, locks the short petals 316b, 316c the tri-pod configuration. Actuation of the slide bolt 352 in the opposite direction reverts the shorts petals 316b, 316c to the stacked configuration beneath the long petal 316a. Two necks 312b may be disposed within slot 312a to lock the slide bolt and the short petals 316b, 316c in either the stacked or tri-pod configurations.

In use and as shown in FIGS. 5A-5C, prior to insertion, slide bolt 352 is positioned accordingly to revert the short petals 316b, 316c in the stacked configuration (FIG. 4A). This reduces the profile of the tissue guard 300 to facilitate insertion. The long petal 316a is then inserted into the incision "I" and slipped through the incision "I" in a manner to pry open the incision "I" like a shoe-horn (FIGS. 5A and 5B). Once seated within the incision "I" with the proximal flange 326 flush against the external side of tissue "T", the surgeon actuates the slide bolt to rotate the short petals 316b, 316c outwardly in the direction "E" to engage opposing sides of tissue "T" within incision "I" (FIG. 5C). The slide bolt 352 is then locked in neck 312b to secure the short petals 316b, 316c (and the long petal 316a) in the tri-pod configuration. This seats the tissue guard 300 within the access device 150 (or in direct contact with tissue) in a more balanced fashion and provides opposing retention for the tissue guard 300 therein. As mentioned above, the shoe-horn or duck-bill shape of the petals 316a, 316b, and 316c facilitate retention of the tissue guard 300 within the access device in the incision "I".

Once secured, the tissue guard 300 may be connected to a smoke evacuation system (not shown) via coupling 720 that attaches to a smoke evacuation hose 710.

Although described for use with an access device 150, tissue guards 200 and 300 may be utilized to directly engage an incision "I" in tissue "T", e.g., See FIGS. 3A-3C and 5A-5C.

From the foregoing and with reference to the various drawings, those skilled in the art will appreciate that certain modifications can be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A tissue guard, comprising:
   a body including a proximal end and a distal end and defining a lumen therethrough, the distal end including a long petal and a short petal disposed in substantial opposition relative to one another, the short petal configured to move between a first position wherein the short petal is disposed within the lumen to facilitate insertion of the long petal within an incision and a second position wherein the short petal is extended relative to the lumen and in substantial opposition to the long petal to facilitate retention of the tissue guard within the incision.

2. The tissue guard according to claim 1, wherein the short petal is selectively invertable within the lumen.

3. The tissue guard according to claim 1, wherein the long petal is shaped like a shoe horn and is configured to pry the incision open upon insertion therein.

4. The tissue guard according to claim 1, wherein the short petal is shaped like a shoe horn when extended relative to the lumen.

5. The tissue guard according to claim 1, wherein the proximal end of the body is configured to remain outside the incision.

6. The tissue guard according to claim 1, wherein after insertion of the long petal within the incision, the short petal is selectively extendible from the lumen to engage tissue opposite the long petal to facilitate retention of the tissue guard.

7. The tissue guard according to claim 6, wherein the short petal is reverted from within the lumen to extend the short petal to engage tissue opposite the long petal to facilitate retention of the tissue guard.

8. The tissue guard according to claim 6, wherein the short petal is rotated from within the lumen to extend the short petal to engage tissue opposite the long petal to facilitate retention of the tissue guard.

9. The tissue guard according to claim 6, wherein the short petal cooperates with a slide bolt disposed in a slot defined within the body of the tissue guard to selectively rotate and extend the short petal to engage tissue opposite the long petal to facilitate retention of the tissue guard.

10. The tissue guard according to claim 9, wherein the slot includes a neck defined therein to lock the slide bolt when the short petal is disposed in one of the first or second positions.

11. The tissue guard according to claim 1, wherein the two short petals are disposed within the lumen when the short petals are disposed in the first position, the short petals disposed in stacked relation relative to one another and the long petal.

12. The tissue guard according to claim 11, wherein the short petals and the long petal form a tri-pod arrangement when the short petals are disposed in the second position.

13. The tissue guard according to claim 1, wherein the tissue guard is made from a biocompatible plastic.

14. The tissue guard according to claim 1, wherein the tissue guard is monolithically formed from a single piece of material having a thickness configured to withstand cutting and puncturing under normal operating conditions.

15. A tissue guard, comprising:
a body including a proximal end and a distal end and defining a lumen therethrough, the distal end including a long petal and a short petal disposed in substantial opposition relative to one another, the short petal configured to move between a first position wherein the short petal is inverted within the lumen to facilitate insertion of the long petal within an incision and a second position wherein the short petal is reverted relative to the lumen and extended in substantial opposition to the long petal to facilitate retention of the tissue guard within the incision.

16. The tissue guard according to claim 15, wherein the long petal is shaped like a shoe horn and is configured to pry the incision open upon insertion therein.

17. The tissue guard according to claim 15, wherein the short petal is shaped like a shoe horn when extended relative to the lumen.

18. The tissue guard according to claim 15, wherein the proximal end of the body is configured to remain outside the incision.

19. The tissue guard according to claim 15, wherein after insertion of the long petal within the incision, the short petal is selectively extendible from the lumen to engage tissue opposite the long petal to facilitate retention of the tissue guard.

20. The tissue guard according to claim 19, wherein the short petal is reverted from within the lumen to extend the short petal to engage tissue opposite the long petal to facilitate retention of the tissue guard.

21. The tissue guard according to claim 20, wherein the short petal is rotated from within the lumen to extend the short petal to engage tissue opposite the long petal to facilitate retention of the tissue guard.

22. The tissue guard according to claim 15, wherein the tissue guard is made from a biocompatible plastic.

23. The tissue guard according to claim 15, wherein the tissue guard is monolithically formed from a single piece of material having a thickness configured to withstand cutting and puncturing under normal operating conditions.

24. A tissue guard, comprising:
a body including a proximal end and a distal end and defining a lumen therethrough, the distal end including a long petal and two short petals, the short petals configured to move between a first position wherein the short petals are disposed within the lumen in stacked relation relative to one another and relative to the long petal to facilitate insertion of the long petal within an incision and a second position wherein the short petals are rotated from within the lumen to extend the short petals to engage tissue opposite the long petal to facilitate retention of the tissue guard.

25. The tissue guard according to claim 24, wherein the short petals and the long petal form a tri-pod arrangement when the short petals are disposed in the second position.

26. The tissue guard according to claim 24, wherein the short petals cooperate with a slide bolt disposed in a slot defined within the body of the tissue guard to selectively rotate and extend the short petals to engage tissue opposite the long petal to facilitate retention of the tissue guard.

27. The tissue guard according to claim 26, wherein the slot includes a neck defined therein to lock the slide bolt when the short petals are disposed in one of the first or second positions.

\* \* \* \* \*